United States Patent
Bojarski

[11] Patent Number: 6,086,591
[45] Date of Patent: Jul. 11, 2000

[54] SOFT TISSUE ANCHOR

[75] Inventor: Raymond A. Bojarski, Attleboro, Mass.

[73] Assignee: Smith & Nephew, Inc., Memphis, Tenn.

[21] Appl. No.: 09/240,227

[22] Filed: Jan. 29, 1999

[51] Int. Cl.[7] .................................................. A61B 17/56
[52] U.S. Cl. .............................. 606/64; 606/62; 606/232; 623/13
[58] Field of Search ............................... 606/62–64, 232; 623/13

[56] References Cited

U.S. PATENT DOCUMENTS 4,870,957  10/1989  Goble et al. .
4,997,433   3/1991  Goble et al. ............................... 606/64
5,098,433   3/1992  Freedland ................................... 606/63

FOREIGN PATENT DOCUMENTS 2 590 792   6/1987   France .

WO 98/22048  5/1998  WIPO .

*Primary Examiner*—Gary Jackson
*Attorney, Agent, or Firm*—Fish & Richardson P.C.

[57] ABSTRACT

An anchor for fixing soft tissue within a bone tunnel includes a distal end sized and shaped for passage through the tunnel and a proximal end for extending into the tunnel. The distal end is constructed to engage bone cortex adjacent the tunnel opening. The proximal end includes a mount for attaching soft tissue to the anchor. The distal end defines a hook having a sharp or rounded tip and teeth for engaging the bone cortex. The mount is a loop through which soft tissue is passed. A method for attaching soft tissue to bone includes passing the anchor through the tunnel, distal end first, and positioning the anchor in the tunnel with the distal end protruding from the tunnel such that the distal end engages bone cortex adjacent the opening of the tunnel and the proximal end extends into the tunnel.

31 Claims, 10 Drawing Sheets

SOFT TISSUE ANCHOR

BACKGROUND OF THE INVENTION

The invention relates to soft tissue anchors.

An increasing number of surgical techniques are now performed arthroscopically. One type of arthroscopic procedure reconstructs the anterior cruciate ligament (ACL) in the knee. Several ACL reconstructive techniques are described in Rosenberg, U.S. Pat. No. 5,139,520, entitled "Method for ACL Reconstruction," which is incorporated herein by reference.

When the ACL has ruptured and is nonrepairable, it is usually replaced in the knee using a substitute graft harvested from the patient or from a donor. Alternatively, artificial grafts formed synthetically or with a combination of artificial and natural material are used. In general, the replacement graft is implanted by securing one end of the graft in a passage formed within the femur, and passing the other end of the graft through a tibial channel and securing it to the tibia adjacent the tibial channel. The graft must be rigidly fixed to the femur and tibia.

Each end of the replacement graft is attached to a fastener, e.g., a fixation screw or button, by suture or tape, as described in Ferragamo, U.S. Pat. No. 5,769,894, entitled "Graft Attachment Device and Method of Attachment," incorporated herein by reference. One fastener is secured to the tibia and the other fastener to the femur to secure the graft in place.

SUMMARY OF THE INVENTION

According to one aspect of the invention, an anchor for fixing soft tissue within a bone tunnel includes a body having a distal end sized and shaped for passage through a bone tunnel and a proximal end for extending into the bone tunnel. The distal end is constructed to engage bone cortex adjacent an opening of the bone tunnel. The proximal end of the body includes a mount for attaching soft tissue to the body.

Embodiments of this aspect of the invention may include one or more of the following features. The distal end defines a hook for engaging bone cortex adjacent the opening of the bone tunnel. The hook has a rounded tip, or, alternatively, the tip of the hook has a sharp point. The hook has an undersurface with one or more teeth for engaging the bone cortex. The distal and proximal ends are connected by a neck. The neck has a hook-facing surface. The undersurface of the hook and the hook-facing surface of the neck define an angle therebetween in the range of about 35 to 45 degrees.

The distal end defines one or more holes for threading suture therethrough. The distal end includes a crown having a generally rounded shape.

The mount is a loop defining an opening for passage of soft tissue therethrough. The loop and the neck are centered along a common longitudinal axis. Alternatively, the center of the loop is offset from the longitudinal axis of the neck. The loop is generally oblong-shaped, or, alternatively, the loop is generally circular in shape. The loop's width is, e.g., greater than or equal to the width of the neck.

The anchor includes a support segment for biasing the hook into engagement with the bone cortex. The support segment is a portion of the distal end and the neck which is movable between a relaxed position in which the support segment portion is displaced from remaining portions of the distal end and the neck, and a loaded position in which the support segment portion is generally parallel with the remaining portions of the distal end and the neck.

The distal end and the neck of the anchor are divided into three axially alignable segments. Alternatively, the distal end and the neck of the anchor are divided into two lateral segments.

According to another aspect of the invention, a method for attaching soft tissue to bone includes forming a tunnel through the bone to receive the soft tissue, attaching soft tissue to the anchor mount, passing the anchor through the bone tunnel, distal end first, and positioning the anchor in the bone tunnel with the distal end protruding from the bone tunnel. The distal end engages bone cortex adjacent the opening of the bone tunnel and the proximal end extends into the bone tunnel.

Embodiments of this aspect of the invention may include one or more of the following features. The distal end of the anchor defines a hook, and the step of positioning includes engaging the hook with bone cortex adjacent the opening of the bone tunnel. The distal end of the anchor defines a hole, and the step of positioning includes threading a suture through the hole and pulling the suture to position the anchor device in the bone tunnel. The anchor mount is a loop, and the step of attaching the soft tissue to the mount includes passing the soft tissue through the loop.

In illustrated embodiments of the invention, the anchor includes a neck connecting the distal end and the mount, and the step of forming the bone tunnel includes forming a first tunnel section for receiving the neck and a second tunnel section for receiving the mount. The length of the first tunnel section is slightly less than the length of the neck. The mount has a width greater than a width of the neck, and the step of forming the bone tunnel includes forming the first tunnel section having a width approximately equal to a width of the neck, and the second tunnel section having a width approximately equal to a width of the mount.

Advantages of the invention may include one or more of the following features. The anchor is a one piece, rigid structure having an integral mount such that the soft tissue is attached directly to the anchor device instead of attaching the soft tissue to the anchor device with suture or tape. The elimination of the need for tape or sutures to attach the soft tissue to the anchor simplifies the surgical procedure and enhances the stability and rigidity of the replacement graft.

Other features and advantages will be apparent from the following detailed description, and from the claims.

DESCRIPTION OF THE PREFERRED EMBODIMENTS

Figure 1:
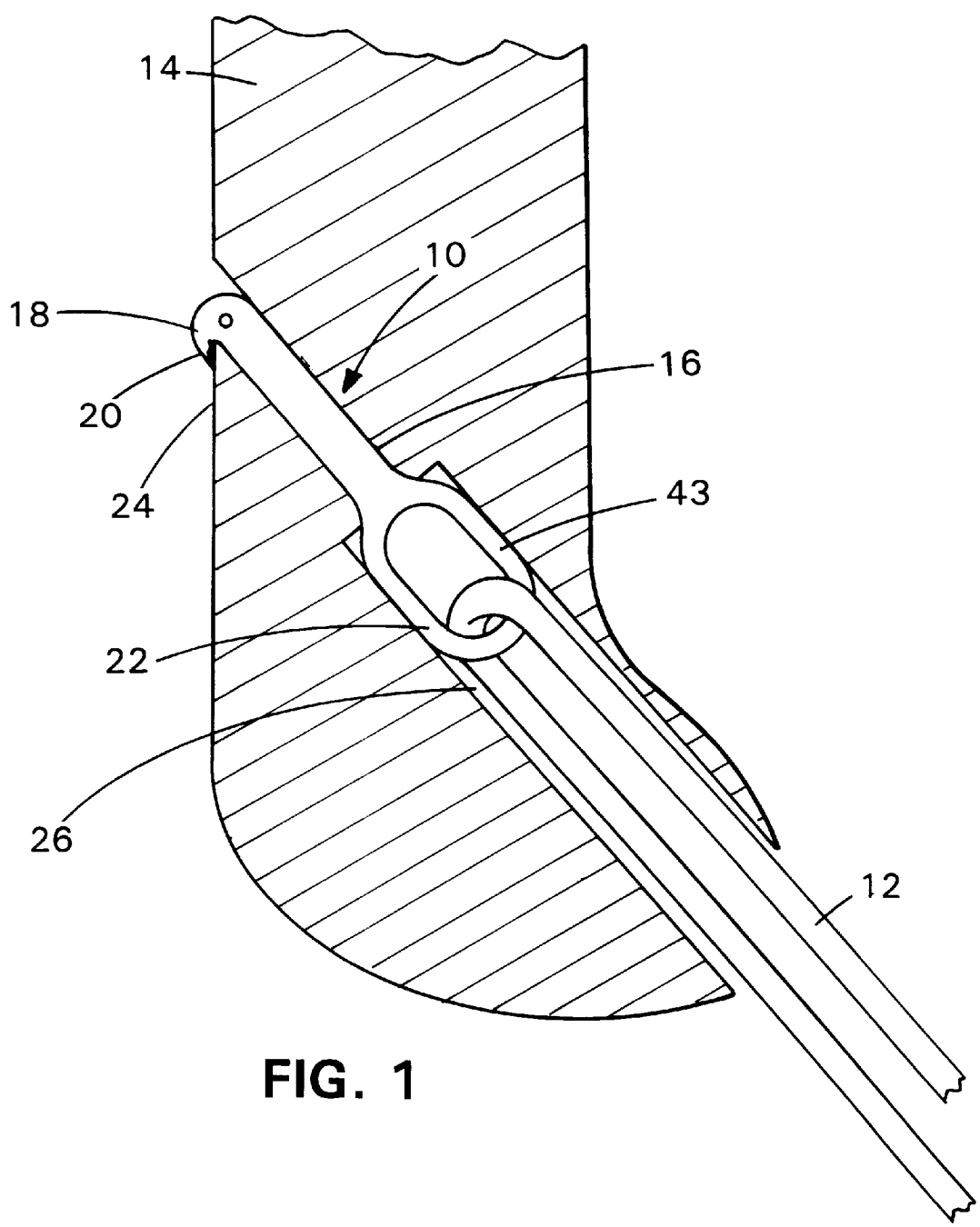
FIG. 1 illustrates an anchor according to the present invention positioned within a bone tunnel.

Referring to FIG. 1, an anchor 10 for attaching soft tissue 12, e.g., a ligament or graft, to bone 14, includes an elongated body 16 having a distal end 18 and a proximal mount 22. Distal end 18 includes a hook 20 for engaging bone cortex 24. Mount 22 is in the shape of a loop 43 for passage of soft tissue 12 therethrough. Soft tissue 12 is secured within a bone tunnel 26 by passing anchor 10, distal end 18 first, through bone tunnel 26, and engaging bone cortex 24 with hook 20.

Figure 2A:
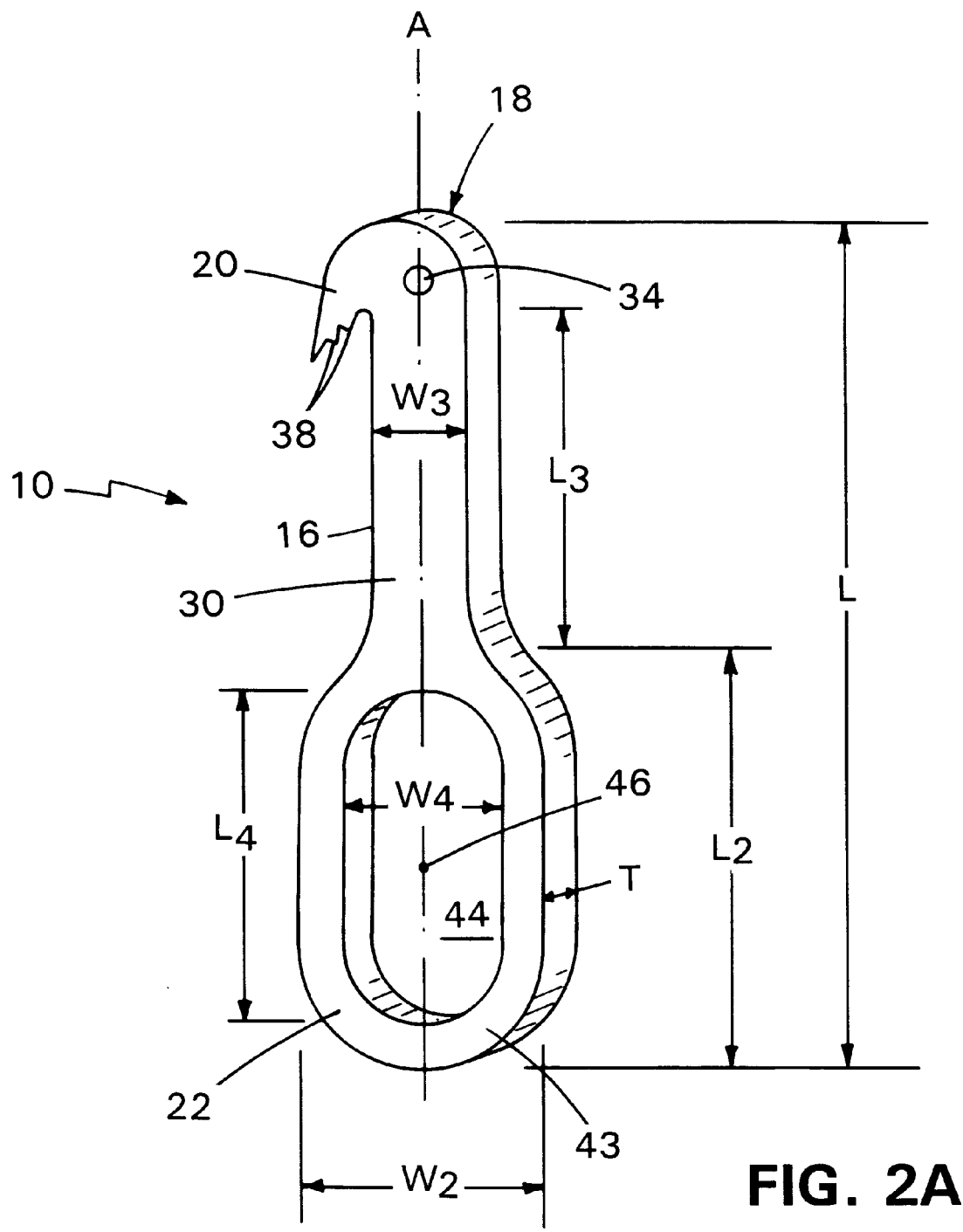
FIG. 2A is an isometric view of the anchor of FIG. 1.
Figure 2B:
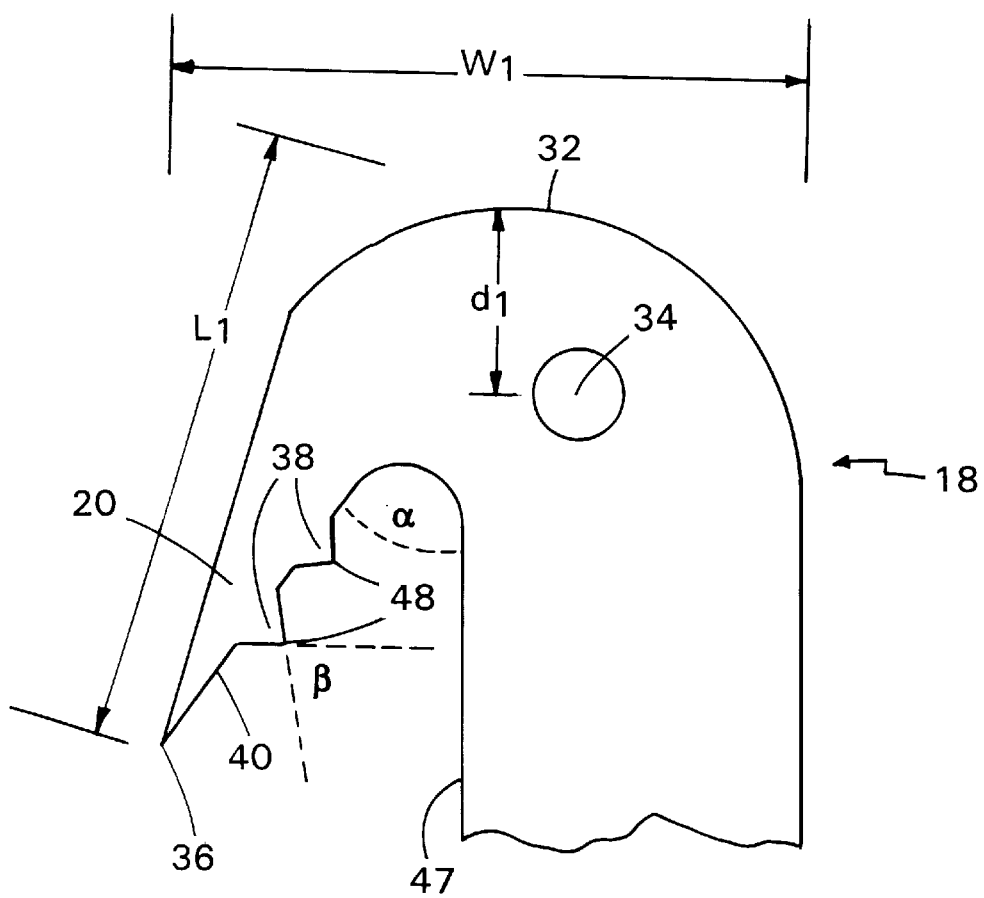
FIG. 2B is a side view of the distal end of the anchor of FIG. 1.

Referring to FIGS. 2A and 2B, body 16 includes an elongated neck 30 connecting distal end 18 and proximal mount 22. Neck 30 defines a central, longitudinal axis, A. Distal end 18 defines a hole 34, for purposes described below, aligned with longitudinal axis, A. Hook 20 extends transversely to longitudinal axis, A. An undersurface 40 of hook 20 and a hook-facing surface 47 of neck 30 define an angle, α, therebetween of, e.g., about 35–45°, preferably about 39°.

Hook 20 includes a bone-engaging tip 36 and one or more bone-engaging teeth 38 located on undersurface 40 of hook 20 (two teeth being shown in FIGS. 2A and 2B). Bone-engaging tip 36 has a radius of, e.g., about 1 mm or less, and each tooth 38 has a pointed end 48 defining an angle, β, of, e.g., about 45°. Alternatively, tip 36 can be pointed to further aid in engaging bone cortex 24. Angle, α, is chosen such that tip 36 and teeth 38 engage bone cortex 24 when anchor 10 is in its final position within bone tunnel 26, as shown in FIG. 1.

Loop 43 is oblong in shape and defines an oblong tissue-receiving opening 44. A center 46 of loop 43 is aligned with longitudinal axis, A.

Anchor 10 is configured to secure hook 20 to bone cortex 24 while positioning neck 30 and loop 43 within bone tunnel 26. Distal end 18 of anchor 10 has a crown portion 32 which is rounded to facilitate entry and passage of anchor 10 through bone tunnel 26, distal end first. Hook 20 is small enough to pass through bone tunnel 26 while being large enough to provide the desired fixation to bone cortex 24.

Figure 3:
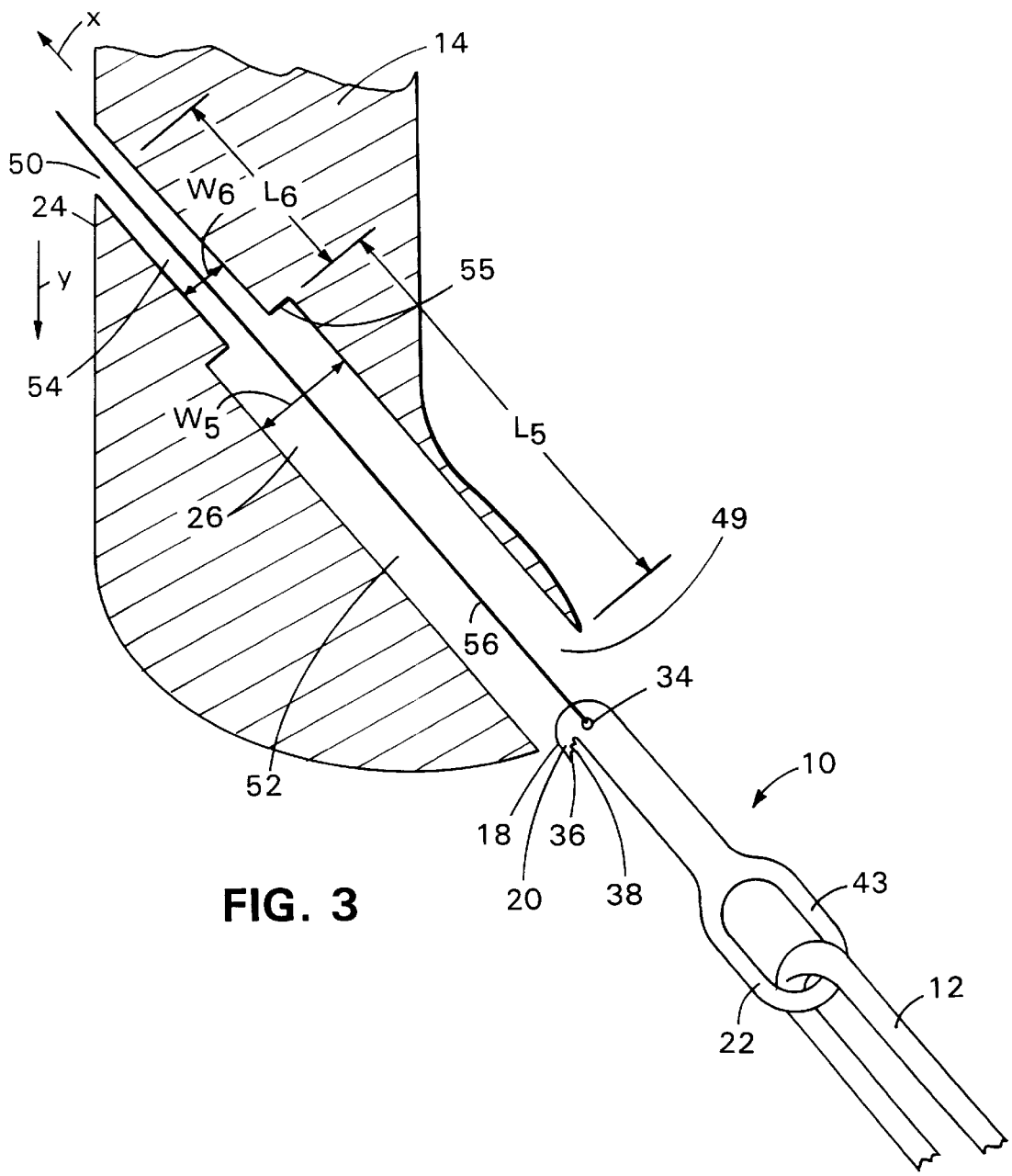
FIG. 3 illustrates insertion of the anchor of FIG. 1 into the bone tunnel.

Distal end 18 has a width $W_1$ of, e.g., about 5 mm, loop 43 has a width $W_2$ of, e.g., about 8 mm, and neck 30 has a width $W_3$ of, e.g., about 3 mm. Referring also to FIG. 3, bone tunnel 26 has a proximal opening 49, a distal opening 50, a first region 52, and a second region 54. A shelf 55 is formed at the juncture of first region 52 and second region 54. First region 52 has a width $W_5$ of, e.g., about 8 mm, which is approximately equal to width $W_2$ of proximal loop 43 to snugly hold loop 43 within first region 52. Second region 54 has a width $W_6$ of, e.g., about 5 mm, which is approximately equal to width $W_3$ of neck 30 to snugly hold neck 30 within second region 54. The widths $W_5$ and $W_6$ of regions 52 and 54 are sized to assist in securely positioning anchor 10 within bone tunnel 26 and to minimize trauma to the patient. In particular, by having the width of neck 30 smaller than the width of loop 43, the width of bone tunnel 26 can be decreased in region 52 which lessens the trauma to the patient.

Loop 43 has a length $L_2$ of, e.g., about 11.7 mm, and neck 30 has a length $L_3$ of, e.g., about 11.4 mm. First region 52 of bone tunnel 26 has a length $L_5$ of, e.g., about 50 mm, which is longer than length $L_2$ of loop 43 such that loop 43 does not protrude from bone tunnel 26. Second region 54 has a length $L_6$ of, e.g., about 8 mm, which is slightly less than length $L_3$ of neck 30 such that with bone-engaging tip 36 protruding from bone tunnel 26, loop 43 is proximal to shelf 55 formed at the juncture of first region 52 and second region 54 of bone tunnel 26.

Hook 20 has a length $L_1$ of, e.g., about 3.5 mm, selected to be long enough to firmly engage bone cortex 24. Hole 34 has a diameter of, e.g., about 1 mm, sized to allow threading of a suture therethrough, and is located a distance $d_1$ of, e.g., about 1.25 mm from crown 32 of anchor 10. Tissue receiving opening 44 of loop 43 is large enough to receive soft tissue 12, having a length $L_4$ of, e.g., about 8.7 mm, and a width $W_4$ of, e.g., about 5.5 mm. Anchor 10 is generally planar in shape, having an overall length, L, of, e.g., about 25 mm and a thickness, T, of, e.g., about 3 mm.

Anchor 10 can be used, for example, for femoral attachment in anterior cruciate ligament (ACL) repair and reconstruction surgery. First, a notchplasty procedure, as described in Rosenberg, supra, is preferably performed to expand the intercondylar notch of the femur bone. Next, bone tunnels are drilled through the tibia and the femur, using any appropriate method, such as the method described in Graf et al., U.S. Pat. No. 5,306,301, entitled "Graft Attachment Device and Method of Using Same," incorporated herein by reference.

Referring particularly to FIG. 3, the surgeon attaches soft tissue graft 12 to loop 43 of anchor 10 by passing graft 12 through opening 44, and attaches suture 56 to anchor 10 by threading suture 56 through hole 34. The surgeon then passes suture 56 through the tunnel formed in the tibia and through bone tunnel 26 formed in the femur, from proximal opening 49 to distal opening 50 of bone tunnel 26.

Next, the surgeon pulls distally on suture 56 (in the direction of arrow, X), causing anchor 10 to pass through the tibia tunnel and into the femur tunnel. The surgeon pulls on suture 56 until distal end 18 protrudes from distal opening 50 of bone tunnel 26. Once hook 20 has emerged from bone tunnel 26, the surgeon pulls laterally on suture 56 (in the direction of arrow, Y), causing tip 36 and teeth 38 of hook 20 to engage bone cortex 24, securing anchor 10 and soft tissue 12 within bone tunnel 26, as shown in FIG. 1.

The surgeon secures the opposite end of graft 12 to the tibia using, e.g., a fixation screw, as described in Ferragamo, supra. Graft 12 is sized such that with both ends of graft 12 secured to bone, graft 12 is placed under tension. The tension in graft 12 aids in providing secure engagement of hook 20 with bone cortex 24.

Alternatively, the surgeon may thread two sutures through hole 34. The surgeon pulls the first suture 56 distally (in the direction of arrow, X) until distal end 18 protrudes from bone tunnel 26, and a second suture (not shown) laterally to engage tip 36 and teeth 38 of hook 20 with bone cortex 24.

Figure 4:
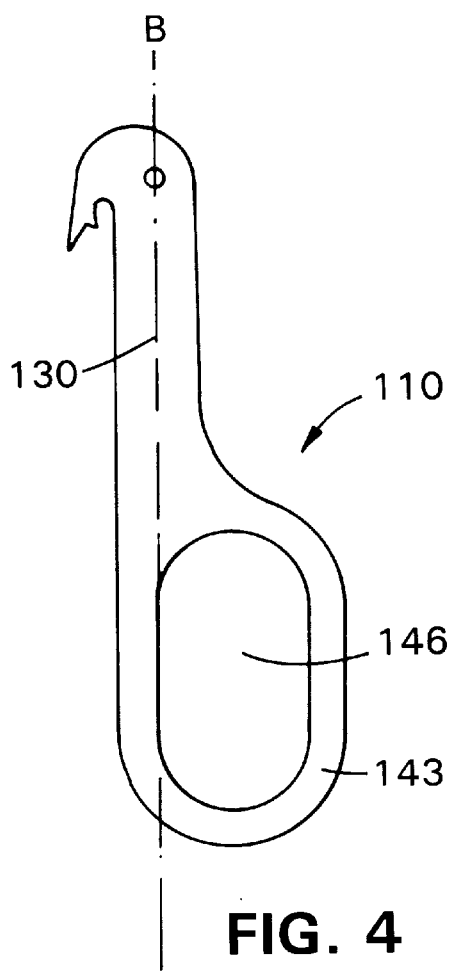
FIGS. 4–6 are side views of alternative embodiments of an anchor.
Figure 5:
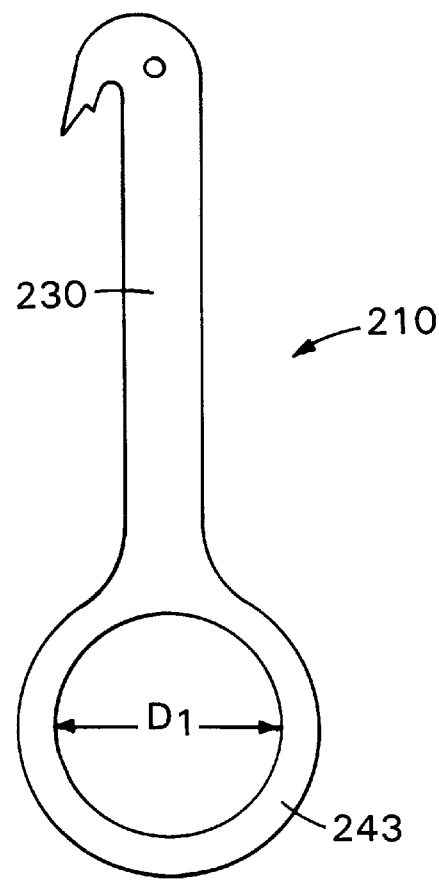
Figure 6:
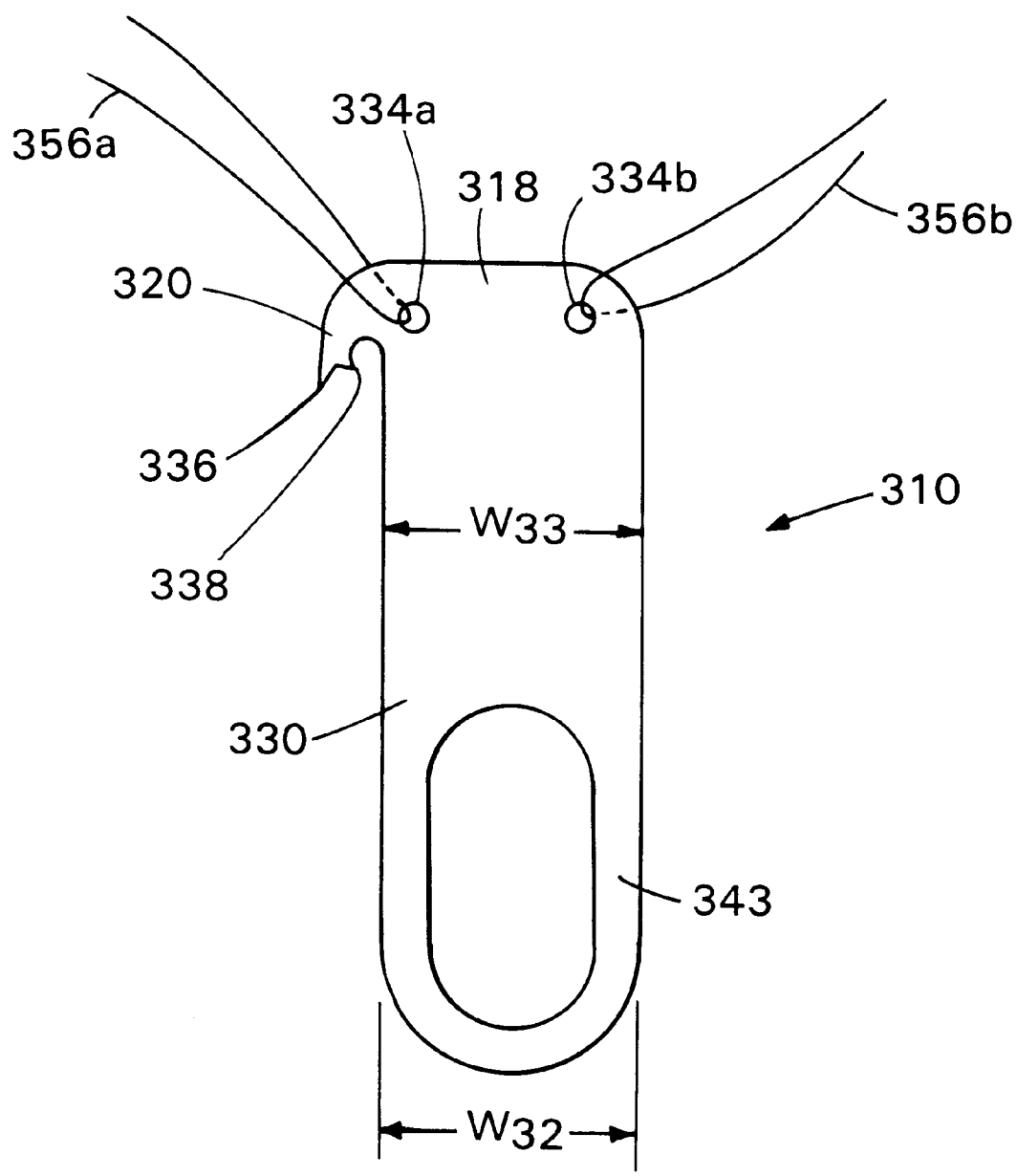

Other embodiments are within the scope of the following claims. For example, referring to FIG. 4, an anchor 110 has a neck 130 and a proximal loop 143. Center 146 of proximal loop 143 is off-set from a central, longitudinal axis, B, defined by neck 130. Referring to FIG. 5, an anchor 210 has a neck 230 and a proximal loop 243 which is circular, rather than oblong. Referring to FIG. 6, an anchor 310 has a distal end 318 defining a hook 320. Hook 320 includes a bone engaging tip 336 and a bone engaging tooth 338. Anchor 310 has a neck 330 with a width, $W_{33}$, about equal to a width, $W_{32}$, of a proximal loop 343.

Distal end 318 further defines two holes 334a and 334b, for threading two sutures 356a and 356b, respectively, therethrough. The surgeon pulls distally on suture 356b until distal end 318 protrudes from bone tunnel 26, and then pulls laterally on suture 356a to secure tip 336 and tooth 338 with bone cortex 24.

Figure 7A:
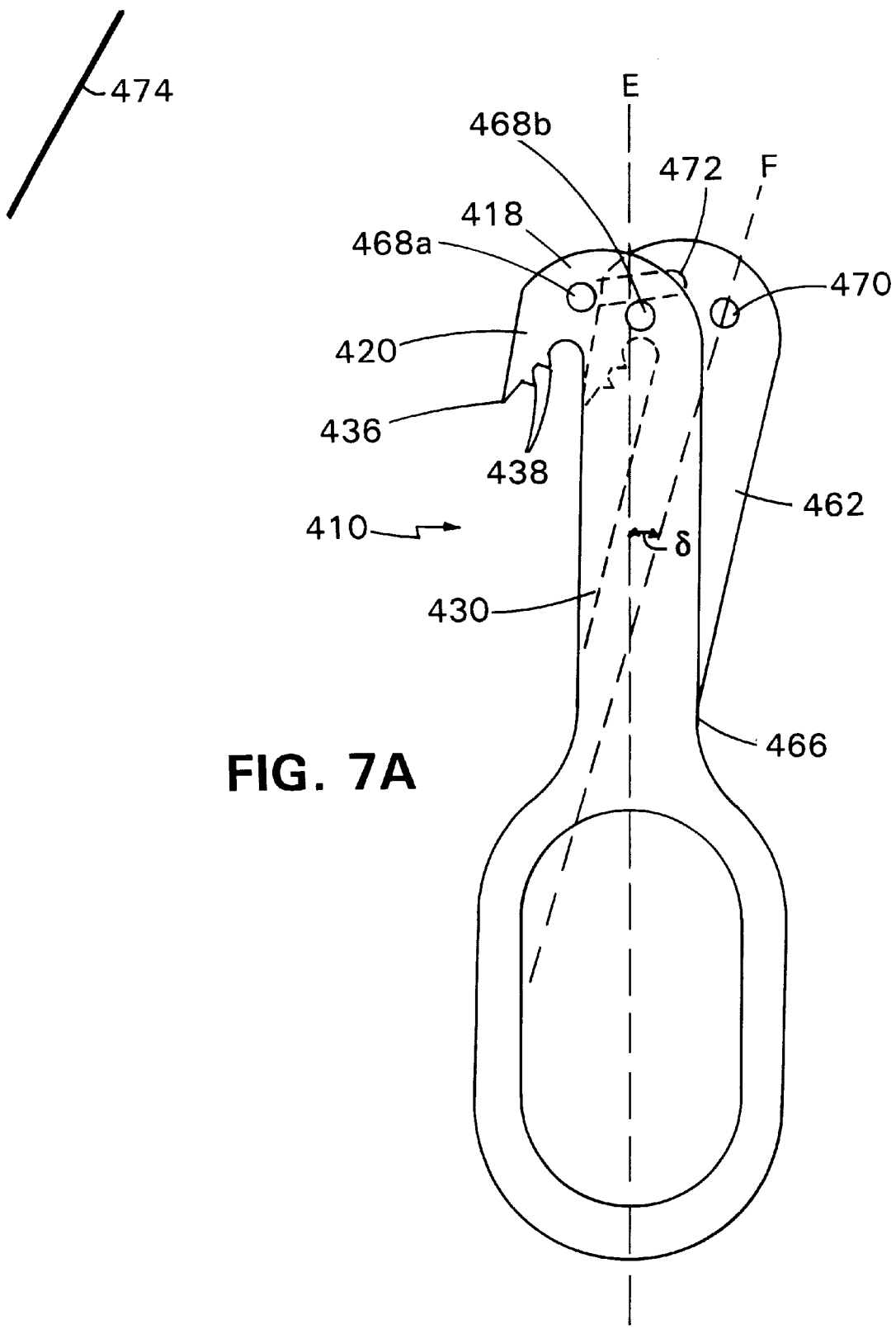
FIG. 7A is a side view of an additional alternative embodiment of an anchor.
Figure 7B:
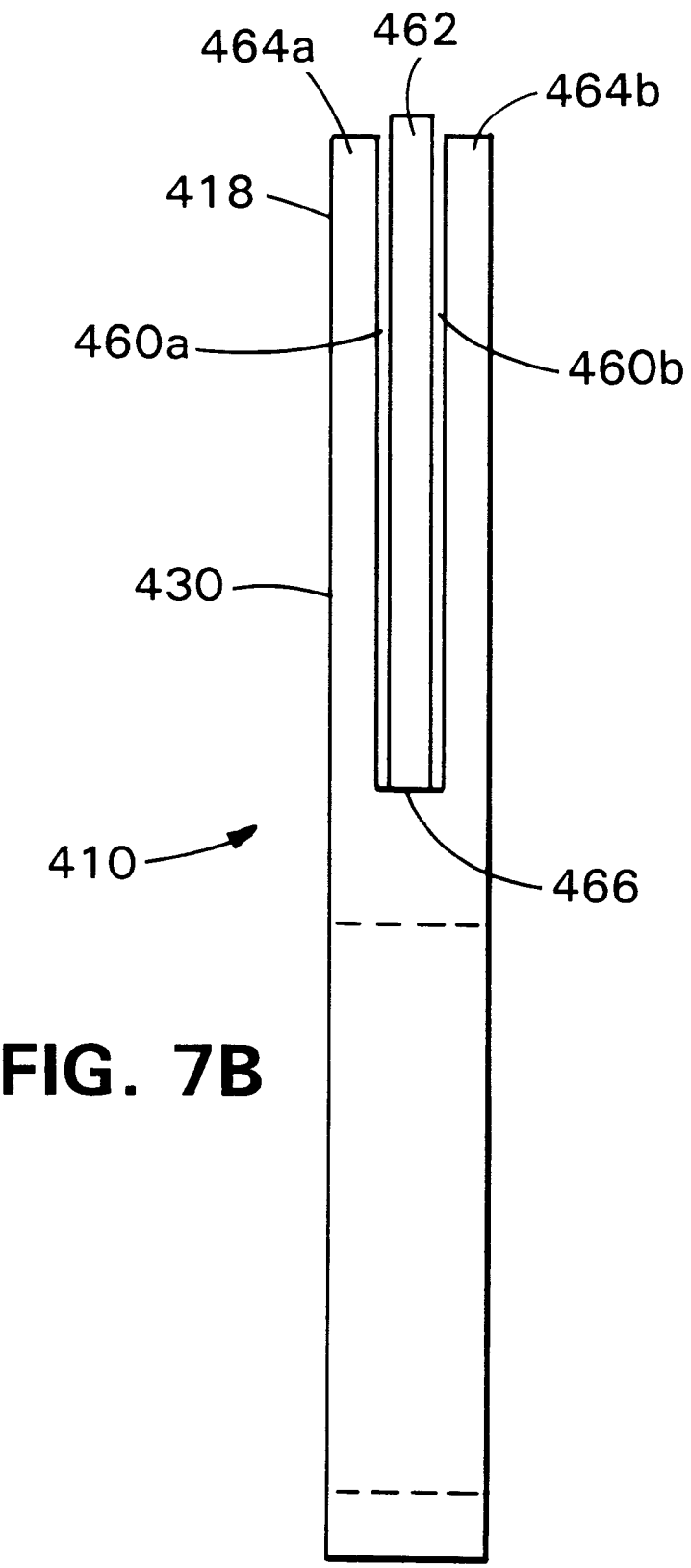
FIG. 7B is a front view of the anchor of FIG. 7A.

Referring to FIGS. 7A and 7B, an anchor 410 has a neck 430 and a distal end 418 divided into three segments 462, 464a, and 464b by slits 460a and 460b. Middle segment 462 is a flexible support segment, while outer segments 464a and 464b are rigid. Flexible support segment 462 is movable between a relaxed position in which segment 462 is biased offset from outer segments 464a, 464b, and a loaded position in which flexible support segment 462 is aligned with outer segments 464a, 464b. When support segment 462 is in its relaxed position, a longitudinal axis, F, of support segment 462 forms an angle, δ, of, e.g., between about 11° and 13°, with a longitudinal axis, E, of outer segments 464a, 464b.

Support segment 462 is formed, e.g., by cutting slits 460a, 460b in anchor 410, deforming support segment 462 into its relaxed position, and heat treating support segment 462 such that support segment 462 is biased toward the relaxed position.

Outer segments 464a, 464b each define two holes, 468a and 468b, and support segment 462 defines a hole 470 and a slot 472. Prior to surgery, segment 462 is bent away from its relaxed orientation toward longitudinal axis E of neck 430, until segment 462 is aligned with outer segments 464a and 464b, and hole 468a is aligned with slot 472 (i.e., δ=0°). A stiff wire 474 is then threaded through holes 468b and 470, holding support segment 462 in place, such that hole 468a and slot 472 remain aligned.

Figure 7C:
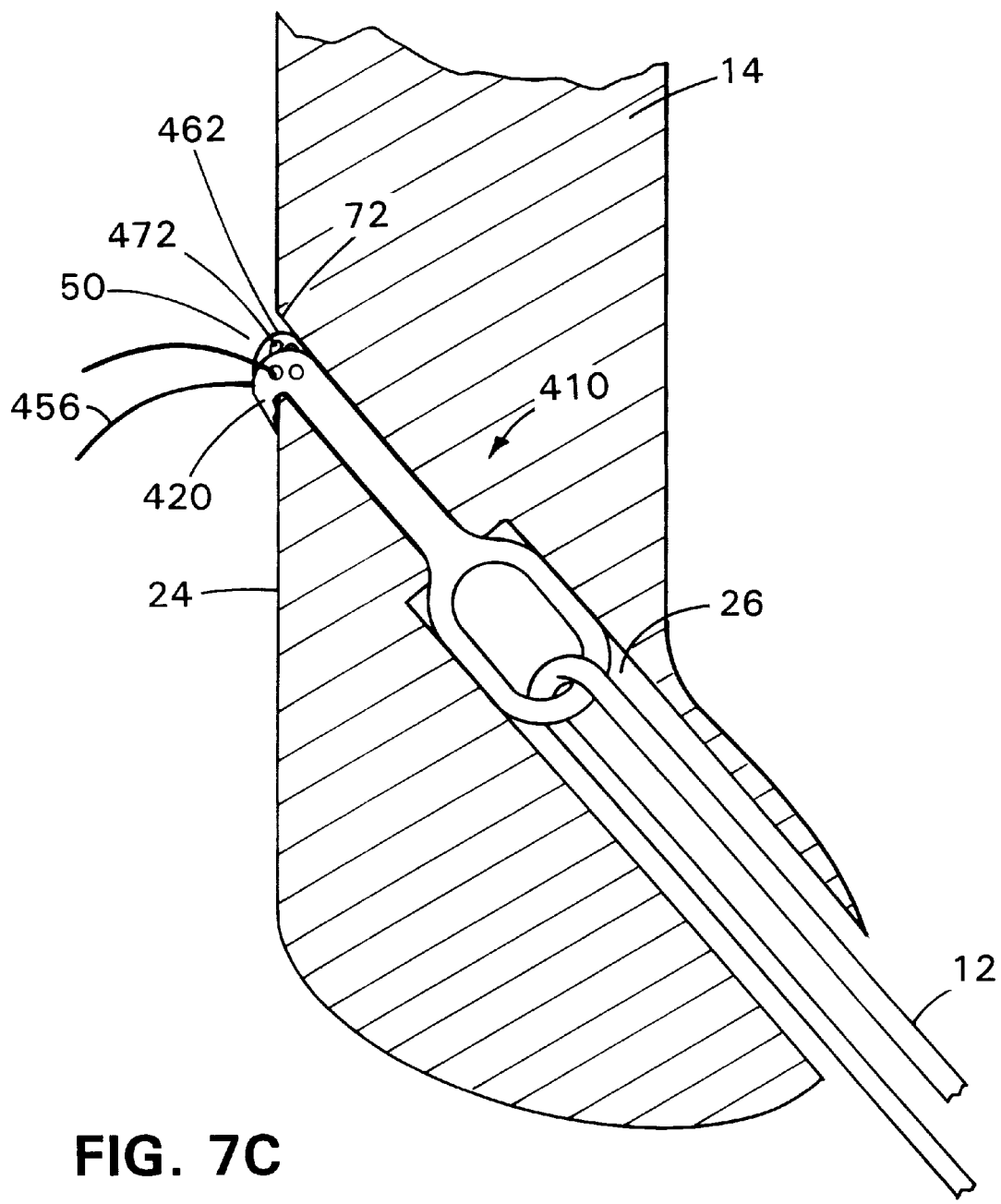
FIG. 7C illustrates the anchor of FIG. 7A positioned within a bone tunnel.

Referring to FIG. 7C, during surgery, a surgeon threads a suture 456 through hole 468a and slot 472, and then pulls on suture 456 to position anchor 410 in place in bone tunnel 26, as described above. Once a tip 436 and pointed teeth 438 of a hook 420 of anchor 410 are engaged with bone cortex 24, the surgeon removes wire 474. When wire 474 is removed, support segment 462 moves toward its relaxed position to abut against a wall 72 of distal opening 50 of bone tunnel 26. The force applied by support segment 462 against wall 72 acts to push hook 420 of outer segments 464a, 464b further into engagement with the bone cortex, helping to hold anchor 410 in place within bone tunnel 26.

Figure 8:
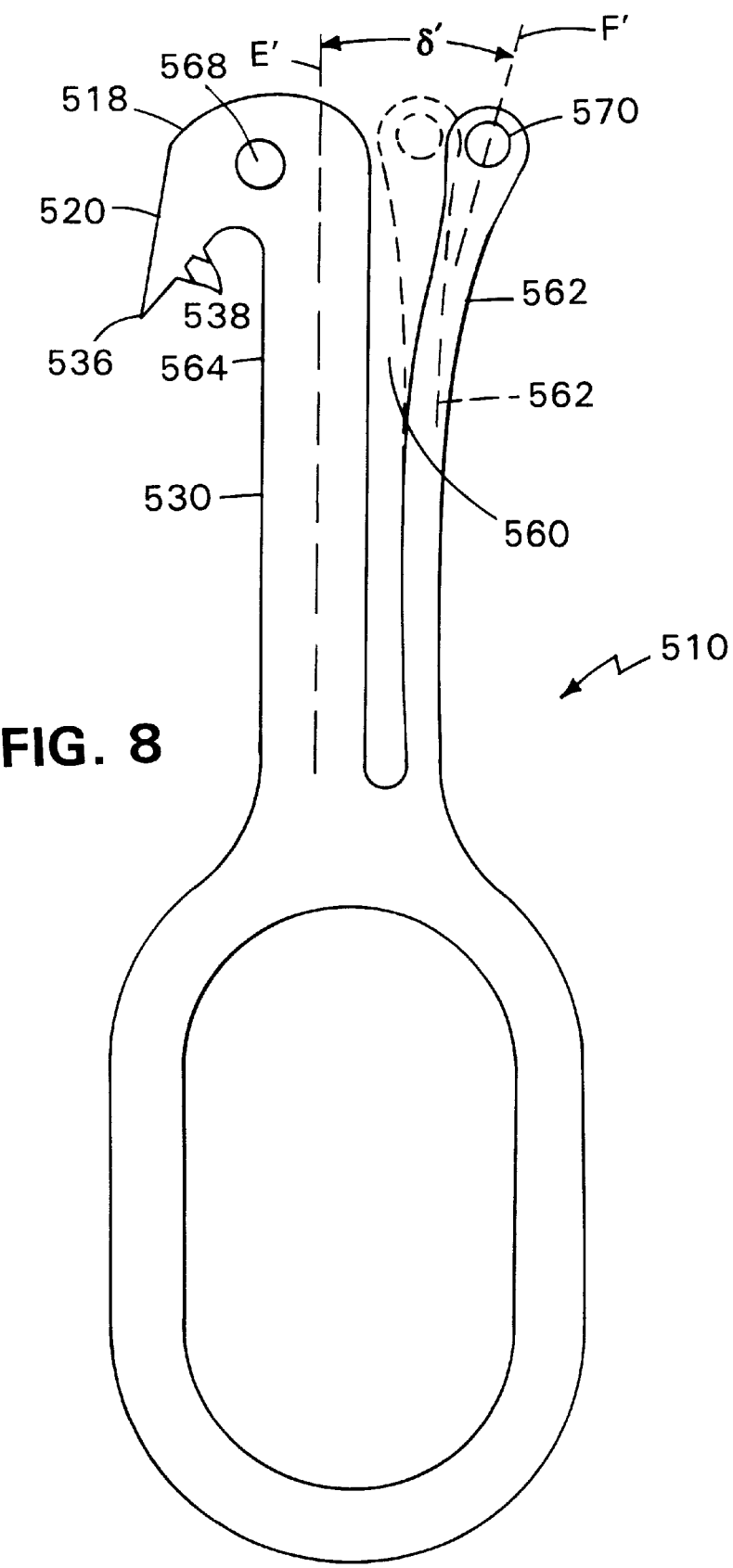
FIG. 8 is a side view of additional alternative embodiment of an anchor.

Referring to FIG. 8, an anchor 510 has a neck 530 and a distal end 518 divided into two lateral segments 562, 564 by a channel 560. Segment 562 is a flexible support segment, while segment 564 is rigid. Flexible support segment 562 is movable between a relaxed position in which segment 562 is biased offset from segment 564, and a loaded position in which flexible support segment 562 is deformed toward segment 564 (shown in dashed line). When support segment 562 is in its relaxed position, an axis, F', of support segment 562 forms an angle, δ', of, e.g., between about 13° and 15°, with a longitudinal axis, E', of segment 564.

Support segment 562 is formed, e.g., by cutting channel 560 in anchor 510, deforming support segment 562 into its relaxed position, and heat treating support segment 562 such that support segment 562 is biased toward the relaxed position.

Segment 564 defines a hole 568, and support segment 562 defines a hole 570. Prior to surgery, support segment 562 is bent away from its relaxed orientation toward longitudinal axis E' of segment 564, until axis F' of support segment 562 is generally parallel with axis E' of segment 564. A stiff wire (not shown) is then threaded through holes 568 and 570, holding support segment 562 in its deformed position.

During surgery, a surgeon threads a suture (not shown) through hole 568, and then pulls on the suture to position anchor 510 in place in bone tunnel 26, as described above. Once a tip 536 and pointed teeth 538 of a hook 520 of anchor 510 are engaged with bone cortex 24, the surgeon removes the wire from holes 568 and 570. When the wire is removed, support segment 562 moves toward its relaxed position to aid in holding anchor 510 in place within the bone tunnel, as described above with reference to FIG. 7C.

Additional modifications of the above embodiments are also possible. For example, the undersurface of the hook can be smooth rather than including one or more teeth. The distal end can define a plurality of holes. The angle, α, defined between the undersurface of the hook and the hook-facing surface of the neck can be varied. In addition, the relative dimensions of the elements of anchors 10, 110, 210, and 310 can be altered. For example, the lengths of the proximal loops can be less than or equal to the lengths of necks, the widths of the proximal loops can be greater than or equal to the widths of the necks, the overall lengths and widths of anchors 10, 110, 210, and 310 can be varied to accommodate different types of surgical procedures and patients with different sized bones, and the lengths of the necks can be varied to accommodate grafts having different lengths. In addition, the width $W_5$ of the first region 52 of bone tunnel 26 can be approximately equal to the width $W_6$ of second region 54, thus eliminating shelf 55.

What is claimed is:

1. A soft tissue anchor for fixing soft tissue within a bone tunnel comprising:
   a rigid body having a distal end and a proximal end, the body extending longitudinally between the distal and proximal ends and being sized to be longitudinally passed through the bone tunnel, the distal end being constructed to engage a bone surface exterior to and adjacent an open end of the bone tunnel with the proximal end of the body extending longitudinally into the bone tunnel, and
   a mount at the proximal end for attaching soft tissue to the body.

2. The anchor of claim 1 wherein the distal end defines a hook for engaging bone cortex adjacent the open end of the bone tunnel.

3. The anchor of claim 2 wherein the hook includes a rounded tip.

4. The anchor of claim 2 wherein the hook includes a sharp-pointed tip.

5. The anchor of claim 2 wherein the hook includes an undersurface having a pointed tooth for engaging bone cortex.

6. The anchor of claim 5 wherein the undersurface of the hook includes a plurality of pointed teeth for engaging bone cortex.

7. The anchor of claim 5 further comprising a neck connecting the distal end and the proximal end, the neck having a hook-facing surface, the undersurface of the hook an the hook-facing surface defining and angle therebetween in the range of about 35 to 45 degrees.

8. The anchor of claim 1 wherein the distal end defines a hole for threading of a suture therethrough.

9. The anchor of claim 8 wherein the distal end defines a plurality of holes for threading of suture therethrough.

10. The anchor of claim 1 wherein the distal end includes a crown having a generally rounded shape.

11. The anchor of claim 1 wherein the mount comprises a loop defining an opening for passage of soft tissue therethrough.

12. The anchor of claim 11 wherein the loop is generally circular in shape.

13. The anchor of claim 11 wherein the loop is generally oblong in shape.

14. The anchor of claim 11 wherein the body further comprises a neck connecting the distal end and the loop.

15. The anchor of claim 14 wherein the loop and the neck are centered along a common longitudinal axis.

16. The anchor of claim 14 wherein a center of the proximal loop is off-set from a longitudinal axis of the neck.

17. The anchor of claim 14 wherein the loop has a width greater than a width of the neck.

18. The anchor of claim 14 wherein the loop has a width approximately equal to a width of the neck.

19. The anchor of claim 1 wherein the body further comprises an elongated neck disposed longitudinally between the distal end and the proximal end for positioning within the bone tunnel.

20. The anchor of claim 19 wherein a longitudinal length of the neck is approximately equal to a longitudinal length of the mount.

21. The anchor of claim 1 wherein the body is a one piece body.

22. The anchor of claim 11 wherein the body further comprises an elongated neck disposed longitudinally between the distal end and the loop, and a longitudinal length of the neck is approximately equal to a longitudinal length of the loop.

23. A soft tissue anchor for fixing soft tissue within a bone tunnel, comprising:
    a distal end sized and shaped for passage through the bone tunnel, the distal end including a hook for engaging bone cortex adjacent an opening of the bone tunnel, the hook including an undersurface having a pointed tooth for engaging bone cortex,
    a proximal end for extending into the bone tunnel, the proximal end including a loop for attaching soft tissue to the body, and
    a neck connecting the distal end and the proximal end, the neck having a hook-facing surface, the undersurface of the hook and the hook-facing surface defining and angle therebetween in the range of about 35 to 45 degrees.

24. A method for attaching soft tissue to bone, comprising:
    forming a tunnel through the bone to receive the soft tissue,
    providing an anchor having a rigid body extending longitudinally between a distal end and a proximal end,
    attaching soft tissue to a mount at the proximal end of the body,
    longitudinally passing the anchor through the bone tunnel, distal end first, and
    positioning the anchor in the bone tunnel with the distal end protruding from the bone tunnel such that the distal end engages a bone surface exterior to and adjacent an open end of the bone tunnel and the proximal end extends into the bone tunnel.

25. The method of claim 24 wherein the distal end defines a hook, and the step of positioning includes engaging the hook with bone cortex adjacent the open end of the bone tunnel.

26. The method of claim 24 wherein the distal end defines a hole, and the step of positioning includes threading a suture through the hole and pulling the suture to position the anchor in the bone tunnel.

27. The method of claim 24 wherein the mount comprises a loop, and the step of attaching the soft tissue to the mount includes passing the soft tissue through the loop.

28. The method of claim 24 wherein the anchor further comprises a neck connecting the distal end and the mount, and the step of forming the bone tunnel comprises forming a first tunnel section for receiving the neck and a second tunnel section for receiving the mount, a length of the first tunnel section being slightly less than a length of the neck.

29. The method of claim 28 wherein the mount has a width greater than a width of the neck, and the step of forming the bone tunnel comprises forming the first tunnel section having a width approximately equal to a width of the neck, and the second tunnel section having a width approximately equal to a width of the mount.

30. A method for attaching soft tissue to bone, comprising:
    forming a tunnel through the bone to receive the soft tissue,
    providing a rigid anchor having a distal end sized and shaped for passage through the bone tunnel, a proximal end for extending into the bone tunnel, and a neck connecting the distal end and the proximal end, the distal end being constructed to engage bone cortex adjacent an opening of the bone tunnel and the proximal end including a mount, the tunnel being formed with a first tunnel section for receiving the neck and a second tunnel section for receiving the mount, a length of the first tunnel section being slightly less than a length of the neck,
    attaching soft tissue to the mount,
    passing the anchor through the bone tunnel, distal end first, and
    positioning the anchor in the bone tunnel with the distal end protruding from the bone tunnel such that the distal end engages bone cortex adjacent the opening of the bone tunnel and the proximal end extends into the bone tunnel.

31. The method of claim 30 wherein the mount has a width greater than a width of the neck, and the step of forming the bone tunnel comprises forming the first tunnel section having a width approximately equal to a width of the neck, and the second tunnel section having a width approximately equal to a width of the mount.

* * * * *